(12) United States Patent
Riepma

(10) Patent No.: US 9,504,650 B2
(45) Date of Patent: Nov. 29, 2016

(54) PHARMACEUTICAL COMPOSITION CONTAINING VITAMIN B12

(71) Applicant: Klaas Alouis Riepma, Valkenburg (NL)

(72) Inventor: Klaas Alouis Riepma, Valkenburg (NL)

( * ) Notice: Subject to any disclaimer, the term of this patent is extended or adjusted under 35 U.S.C. 154(b) by 0 days.

(21) Appl. No.: 14/647,914

(22) PCT Filed: Nov. 28, 2013

(86) PCT No.: PCT/NL2013/050860
§ 371 (c)(1),
(2) Date: May 28, 2015

(87) PCT Pub. No.: WO2014/084736
PCT Pub. Date: Jun. 5, 2014

(65) Prior Publication Data
US 2015/0306033 A1    Oct. 29, 2015

(30) Foreign Application Priority Data

Nov. 30, 2012  (NL) .................................... 2009918
Mar. 30, 2013  (NL) .................................... 2010550

(51) Int. Cl.
*A61K 31/714*  (2006.01)
*A61K 47/44*   (2006.01)
*A61K 9/00*    (2006.01)
*A61K 9/10*    (2006.01)

(52) U.S. Cl.
CPC .............. *A61K 9/10* (2013.01); *A61K 9/0043* (2013.01); *A61K 31/714* (2013.01); *A61K 47/44* (2013.01)

(58) Field of Classification Search
None
See application file for complete search history.

(56) References Cited

U.S. PATENT DOCUMENTS

| 5,801,161 A | 9/1998 | Merkus |
| 2002/0022052 A1 | 2/2002 | Dransfield |
| 2012/0157536 A1* | 6/2012 | Shah .................... A61K 31/196 514/567 |

FOREIGN PATENT DOCUMENTS

| EP | 0735859 B1 | 7/1997 |
| WO | 2007022345 A2 | 2/2007 |

OTHER PUBLICATIONS

Pray, Preventing and Treating Cold Sores, US Pharmacist 2007; 32(4): 16-23.*
How to Use Nose Drops, Internet article, patient.info/health/how-to-use-nose-drops, Oct. 18, 2013.*
M.E. Aulton, Pharmaceutics, "The Science of Dosage Form Design"; p. 265; 1988.
D.Z.B. van Asselt, et al., "Nasal Absorption of Hydroxocobalamin in Healthy Elderly Adults", Br J Clin Pharmacol, 45, 1998, pp. 83-86.

* cited by examiner

*Primary Examiner* — Layla Berry
(74) *Attorney, Agent, or Firm* — Hoffmann & Baron, LLP

(57) ABSTRACT

A pharmaceutical composition for intranasal administration for human subjects includes vitamin B12 and a pharmaceutically acceptable carrier. The vitamin B12 particles are dispersed in a hydrophobic continuous phase as the pharmaceutically acceptable carrier. The dispersion of solid vitamin B12 particles (crystals or amorphic) in a hydrophobic continuous phase displays very satisfactory bioavailability. Also, the intense red color is reduced significantly, making the pharmaceutical composition acceptable for intranasal use.

8 Claims, 4 Drawing Sheets

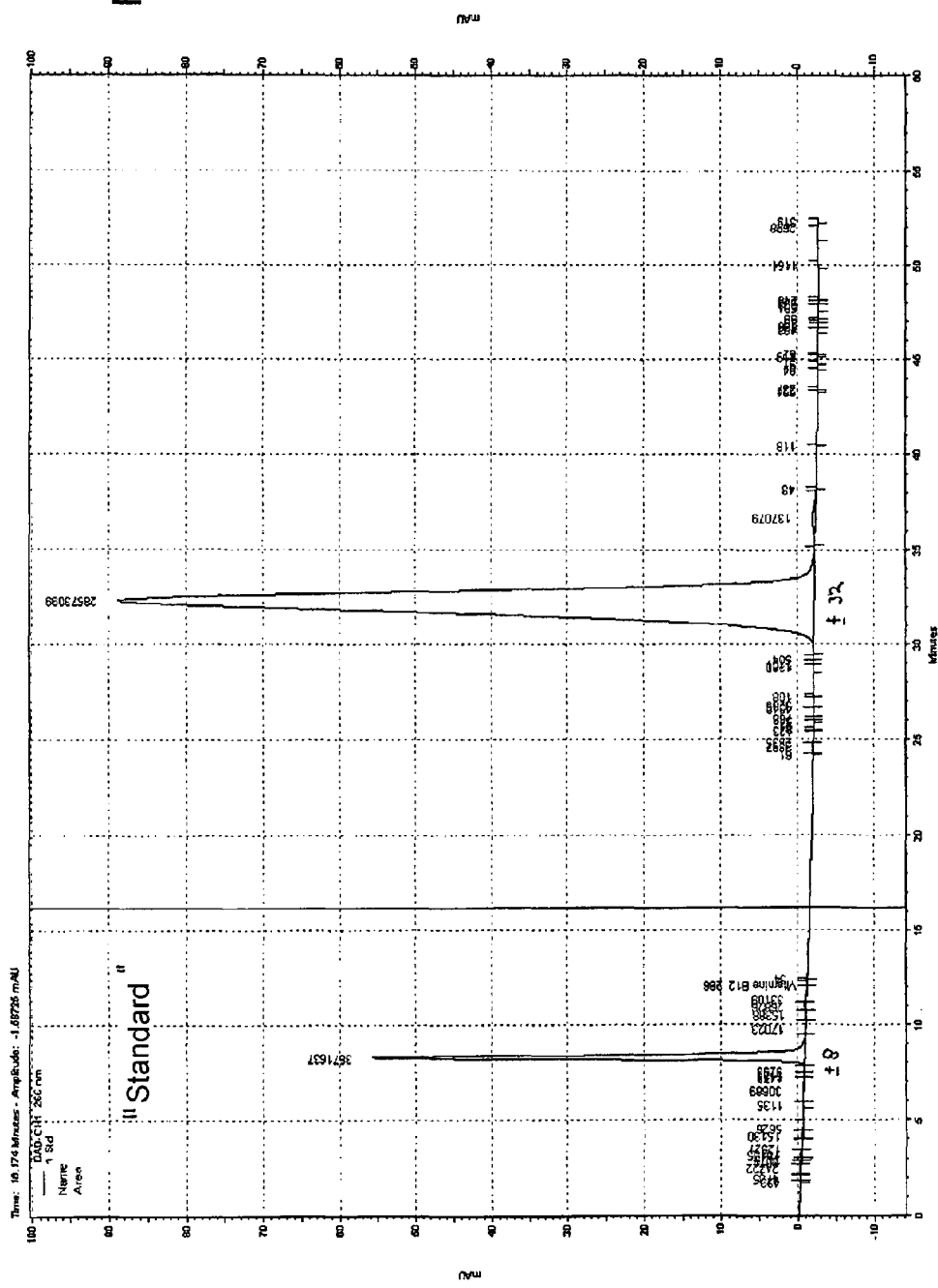

PHARMACEUTICAL COMPOSITION CONTAINING VITAMIN B12

CROSS-REFERENCE TO RELATED APPLICATIONS

This application is the National Stage of International Application No. PCT/NL2013/050860 filed Nov. 28, 2013, which claims the benefit of Netherlands Application Nos. 2009918, filed Nov. 30, 2012, and 2010550, filed Mar. 30, 2013, the contents of all of which are incorporated by reference herein.

FIELD OF THE INVENTION

The present invention relates to a pharmaceutical composition for intranasal administration to a human subject comprising vitamin B12 and a pharmaceutically acceptable carrier.

BACKGROUND OF THE INVENTION

Vitamin B12 is a vitamin that plays a role in mammalian growth, hematopoiesis, production of epithelial cells and maintenance of the nervous system. It is quite water-soluble and thus could be expected to be easily available to human subjects. However, the absorption from the gut of normal dietary amounts of vitamin B12 is believed to be dependent on gastric Intrinsic Factor (GIF), and the loss of Intrinsic Factor leads to vitamin B12 deficiency. The loss of ability to absorb vitamin B12 (B12) is the most common cause of adult B12 deficiency. Such a loss may, for example, be due to pernicious anemia (with loss of Intrinsic Factor) or to a number of other conditions that decrease production of gastric acid, which also plays a part in absorption of B12 from foods. Deficiency is most significantly linked to inadequate absorption rather than low consumption, as those who consume high amounts of vitamin B12 may still experience deficiency as evidenced by a low blood concentration. Vitamin B12 deficiency results in various undesirable conditions such as fatigue, depression, poor memory, etc. [Source: Wikipedia]. Other causes of vitamin B12 deficiency include atrophic gastritis (a thinning of the stomach lining), surgery in which part of the stomach and/or small intestine is removed, conditions affecting the small intestine (such as Crohn's disease, celiac disease, bacterial growth, or a parasite), excessive alcohol consumption, autoimmune disorders (such as Graves' disease or systemic lupus erythematosus) and drug abuse.

Pharmaceutical compositions containing vitamin B12 according to the preamble are known in the art, for example from U.S. Pat. No. 5,801,161 to Merkus, which discloses an intranasal spray. Such a pharmaceutical composition is brightly red, with as the concomitant disadvantage that any fluid of the pharmaceutical composition running from the nose will give the appearance of a bloody nose. Further prior art includes i) Nascobal, a nasal solution of cyanocobalamin available in the USA, and ii) (Br. J. Clin. Pharmacol, 1998, January, 45(1): 83-86 to Asselt et al, showing that hydroxocobalamin nasal sprays are effective in treating vitamin B12 deficiency in elderly adults.

SUMMARY OF THE INVENTION

The object of the present invention is to provide a pharmaceutical composition for intranasal administration with good bioavailability of the active ingredient and with reduced colour intensity by vitamin B12.

To this end, a pharmaceutical composition according to the preamble is characterized in that vitamin B12 particles are dispersed in a hydrophobic continuous phase as the pharmaceutically acceptable carrier.

Surprisingly it has been found that such a dispersion of solid vitamin B12 particles (crystalline or amorphic) in a hydrophobic continuous phase displays very satisfactory bioavailability. Also, the intense red colour is reduced significantly. The pharmaceutical composition may be in the form of an ointment, a nasal spray or nose drops. In the present application, the term vitamin B12 includes cyanocobalamin, hydroxo-cobalamin, methyl-cobalamin, 5'-deoxyadenosyl-cobalamin, aquacobalamin, glutathionyl-cobalamin and nitrilocobalamin, including the pharmaceutically acceptable salts thereof. In general, the concentration of vitamin B12 in the pharmaceutical composition is between 0.01-25 wt./vol. %.

According to a favourable embodiment, the pharmaceutically acceptable carrier is chosen from at least one of i) fat, ii) fatty acids, and iii) wax.

Thus, a hydrophobic environment for vitamin B12 is provided. In general, the fatty acids have a length of the carbon chain of at least 6.

According to a favourable embodiment, pharmaceutically acceptable carrier is oil.

Such a liquid pharmaceutical composition is convenient to administer and to result in high adsorption of vitamin B12 based on concentration in the blood of a human subject.

According to a favourable embodiment, the pharmaceutically acceptable carrier is an anhydrous pharmaceutically acceptable carrier.

This promotes the release of vitamin B12 from the pharmaceutically acceptable carrier. Anhydrous means within the context of the present invention means a water content of less than 5 wt./wt. %, preferably less than 1 wt./wt. % and more preferably with less than 0.2 wt./wt. %.

According to a favourable embodiment, the pharmaceutical composition comprises methylcobalamin or a pharmaceutically acceptable salt thereof as vitamin B12.

Methylcobalamin is considered a powerful drug but because it decomposes easily this value has not been realized in intranasal pharmaceutical compositions according to the prior art as it can't be stored or pharmaceutical compositions have to be kept frozen. The hydrophobic pharmaceutical composition according to the present invention will benefit from improved stability, in particular for methylcobalamin. Without wishing to be bound to any particular theory, it is believed that the fact that vitamin B12 is present as particles reduces its sensitivity to degradation. It is preferred that at least 25 wt. % of vitamin B12 is methylcobalamine or a pharmaceutically acceptable salt thereof.

According to a favourable embodiment, the concentration of vitamin B12 is in the range of 0.05-10 wt./vol. % preferably between 0.4-8 wt./vol. %.

A typical concentration will be, for example, 1000 µg per dose of 100 µl. Generally, the amount administered to a nose will be 50-150 µl of the pharmaceutical composition per nostril, as more would run out of the nose and not be effective.

According to a favourable embodiment, vitamin B12 is colloidally dispersed.

Such a pharmaceutical composition is stable for longer periods.

The present invention also relates to vitamin B12 dispersed in a hydrophobic continuous phase, for use in the intranasal treatment of vitamin B12 deficiency.

The preferred embodiments discussed above are equally applicable to this use, are included by reference for this use, and are not repeated for the sake of brevity only. It has been found that such a dispersion of solid vitamin B12 particles (crystalline or amorphic) in a hydrophobic continuous phase displays very satisfactory bioavailability. Also, the intense red colour is reduced significantly. The vitamin B12 deficiency is any condition where an increased level would be of benefit to the subject. It may be a condition chosen from autism spectrum disorder, fatigue, memory deficiency, ALS, Alzheimer, deficiency caused by drug abuse, thinning of the stomach lining, vitamin B12 deficiency after surgery in which part of the stomach and/or small intestine is removed, Crohn's disease, celiac disease, Graves' disease, systemic lupus erythematosus and migraine.

Finally, the present invention relates to a method of treating a human subject suffering from a condition chosen from autism spectrum disorder, fatigue, memory deficiency, ALS, Alzheimer, deficiency caused by drug abuse, thinning of the stomach lining, vitamin B12 deficiency after surgery in which part of the stomach and/or small intestine is removed, Crohn's disease, celiac disease, Graves' disease, systemic lupus erythematosus and migraine, wherein a pharmaceutical composition according to any of the claims 1 to 7 is administered intranasally.

The method avoids what would appear like a bloody nose due to the intense red colour of vitamin B12.

BRIEF DESCRIPTION OF THE DRAWINGS

The invention will now be illustrated with reference to the example section below, and with reference to the drawings wherein FIGS. 2a to 2c show HPLC chromatograms of a stability experiment with methylcobalamin.

DETAILED DESCRIPTION OF THE INVENTION

Example 3

3.1 Preparation of Stocks

The stability of methylcobalamin is sesame oil was investigated, using an aqueous solution as a control.

a) 100 ml of a 2 w/v % suspension of methylcobalamin in sesame oil was prepared (without stabilizer).

b) Control: 100 ml of a 2 w/v % solution of methylcobalamin was prepared in purified water (grade: for injection purposes. Purchased). 0.1% potassium sorbate was used as a preservative.

3.1 Storage

Both preparations were stored for 6 weeks in a brown PET bottle at room temperature. The concentration methylcobalamin was determined as indicated below.

3.2 Assay

Sample Preparation:
3.2.1 The aqueous solution was pre-processed as disclosed in the Japanese Pharmacopoeia Ed. XV (page 844-845).

3.2.2 The methylcobalamin suspension was extracted with 2×25 ml purified water (grade: for injection purposes). The remaining oil did not contain further vitamin B12, as evidenced by the absence of colour.

Figure 2B:
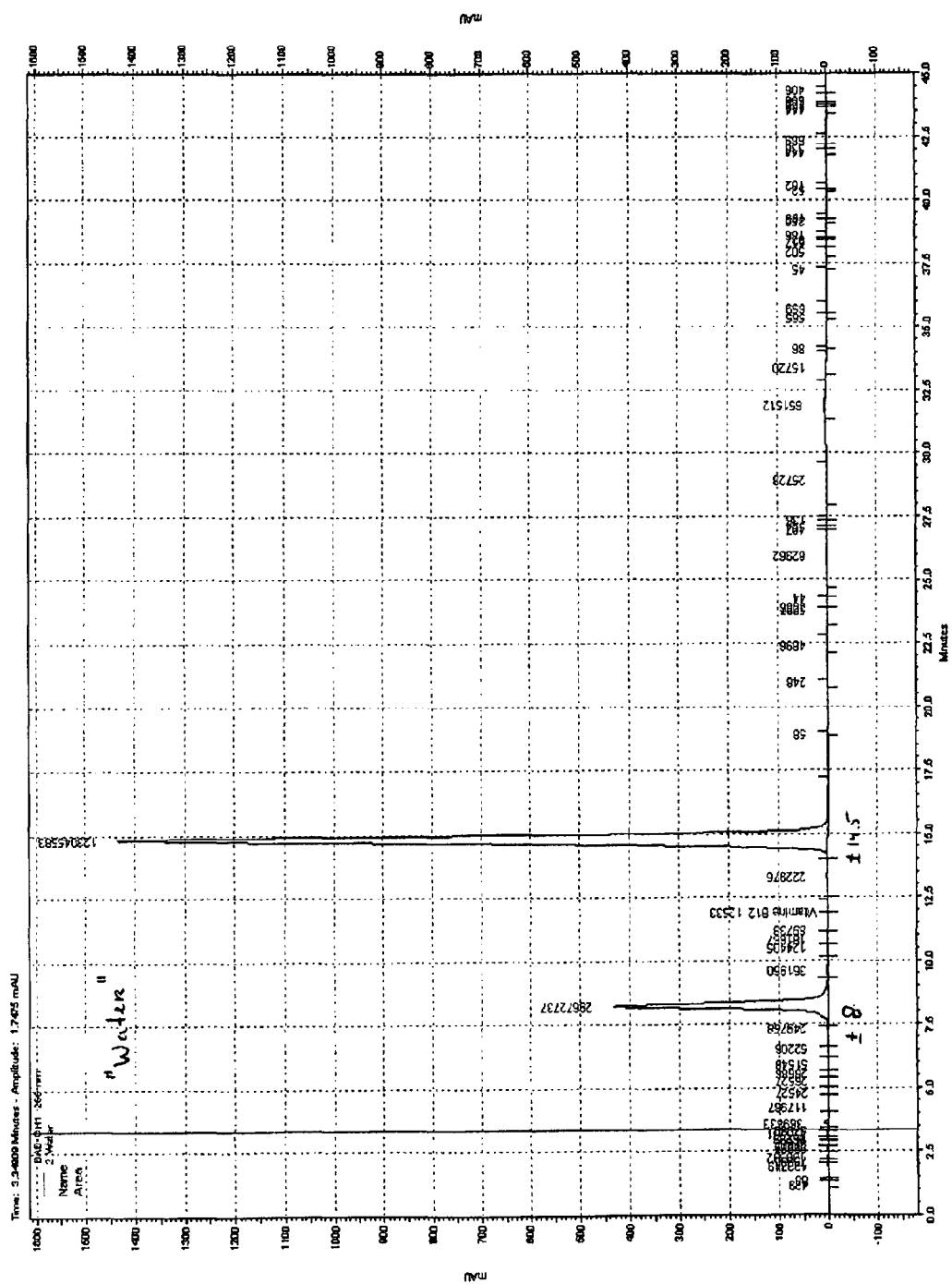
Figure 2C:
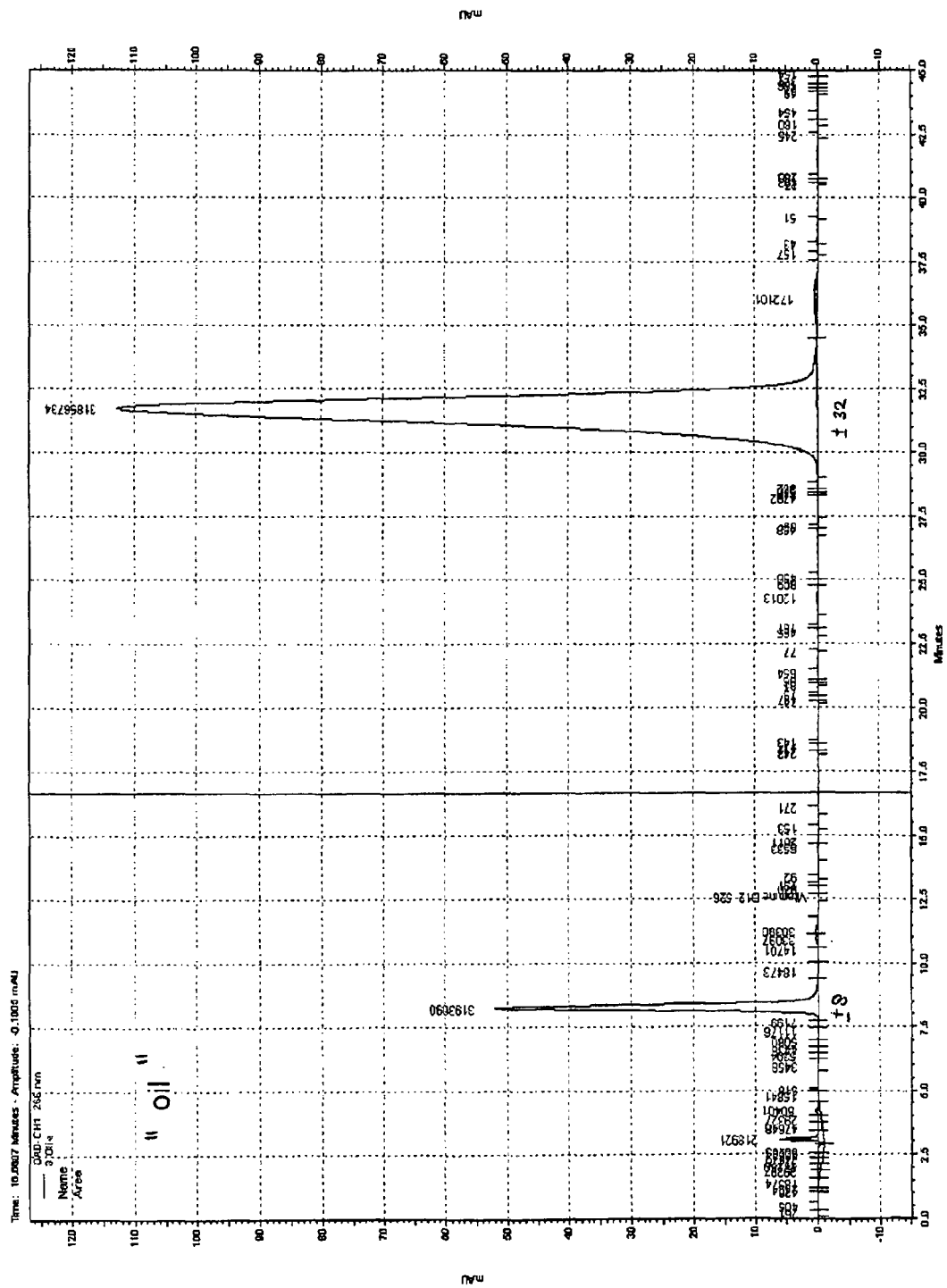

The assay was performed as disclosed in the Japanese Pharmacopoeia Ed. XV (page 844-845), using octasulphonic acid as eluent. A freshly prepared solution was used as the standard, which resulted in two peaks (after 8' and 32'), as shown in FIG. 2a. The control resulted in a main peak at 14.5', none after 32' (FIG. 2b). Methylcobalamin stored in sesame oil resulted in a chromatogram identical to the standard (FIG. 2c).

3.3 Conclusion

Although the peak at 8' is unknown, the experiment shows that methylcobalamin displays excellent stability under these conditions.

Example 1

Cyanocobalamin was reduced in size using a pestle and mortar. A suspension was prepared in sesame-oil in a concentration of 1500 µg per 100 microliter.

The dosage given administered as one spray in nostril and deeply inhaled. In each nostril one spray of 100 µl was given. Subject A received a total dose of 200 µl. Subject B (control) received the same amount of sesame oil without Cyanocobalamin. Blood samples were taken at times 0, and every hour after inhalation. Vitamin B12 was measured using a competitive enzyme immunoassay method.

Vitamin B12

| t (h) | | | | avg. | sd. | Rsd. |
|---|---|---|---|---|---|---|
| | K (pmol/l) | | | | | |
| 0 | 646 | 676 | 673 | 665.0 | 16.52 | 2.5 |
| 1 | 2912 | 2800 | 2888 | 2866.7 | 58.97 | 2.1 |
| 2 | 2768 | 2640 | | 2704.0 | 90.51 | 3.3 |
| 3 | 2116 | 2160 | 2191 | 2155.7 | 37.69 | 1.7 |
| 4 | 1989 | 2107 | 2059 | 2051.7 | 59.34 | 2.9 |
| 5 | 1895 | 1990 | 1871 | 1918.7 | 62.93 | 3.3 |
| 6 | 1980 | 1830 | 1836 | 1882.0 | 84.92 | 4.5 |
| | M (pmol/l) | | | | | |
| 0 | 272 | 312 | 302 | 295.3 | 20.82 | 7.0 |
| 1 | 253 | 284 | 319 | 285.3 | 33.02 | 11.6 |
| 2 | 324 | 298 | 314 | 312.0 | 13.11 | 4.2 |
| 3 | 286 | 307 | 313 | 302.0 | 14.18 | 4.7 |
| 4 | 321 | 315 | 298 | 311.3 | 11.93 | 3.8 |
| 5 | 292 | 302 | 317 | 303.7 | 12.58 | 4.1 |
| 6 | 267 | 288 | 273 | 276.0 | 10.82 | 3.9 |

Figure 1:
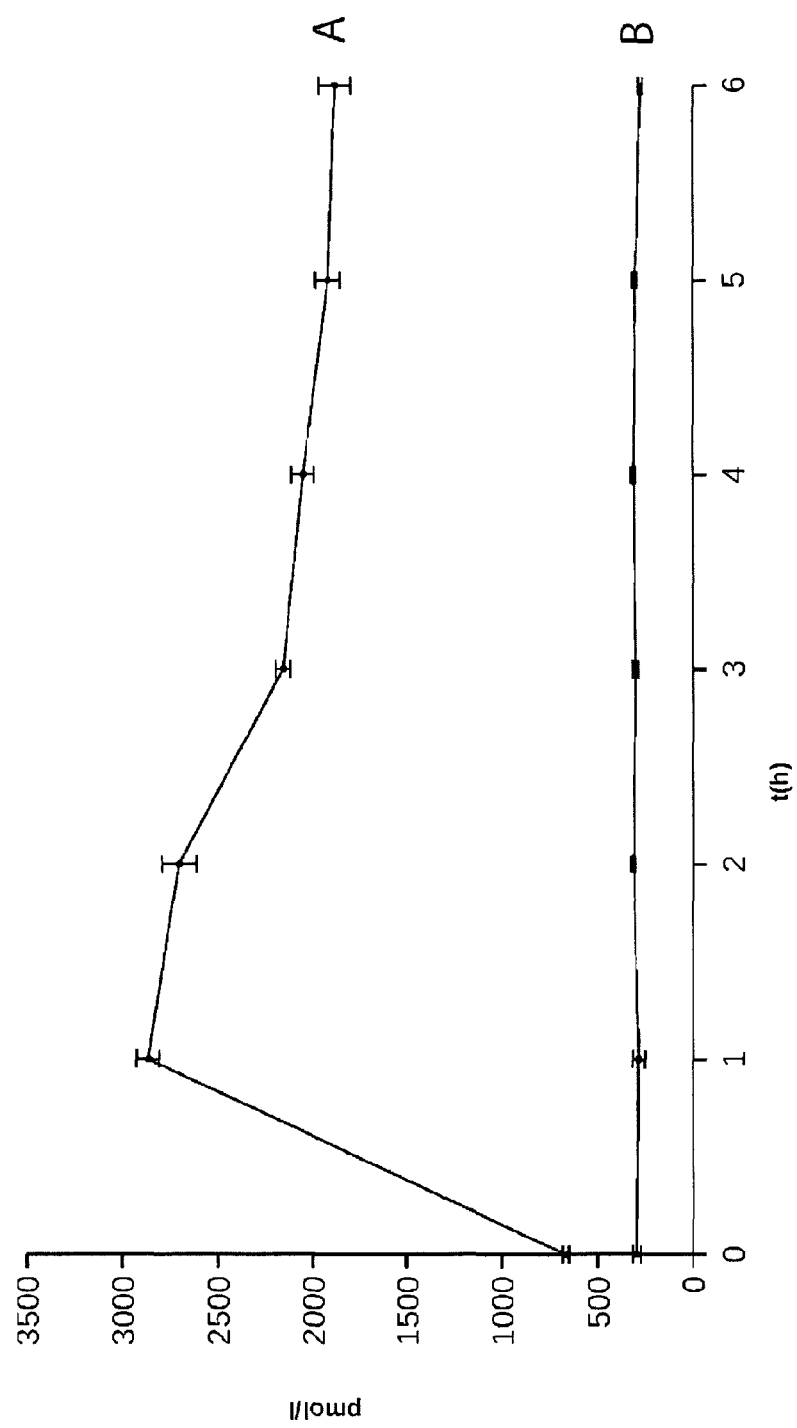
FIG. 1 shows a graph with experimental data after administration of a nasal dose of a pharmaceutical composition according to the invention.

These data are graphically presented in FIG. 1. As can be seen in the figure the concentration increased up to almost 3000 pmol/l. Such a high concentration is believed not to have been reported in the literature before for the nasal absorption of cyanocobalamin. Next to none red fluid was discharged from the nose after administration to subject A. Both the pharmaceutical composition and the control were tolerated well by both subjects.

Example 2

The experiment of Example 1 was repeated with hydroxocobalamin HCl. A suspension was prepared of 1.5% by w/v hydroxocobalamine in sesame oil. A male subject (52 years) received a single droplet of this suspension in each nostril, and then inhaled. Total amount 200 μl.

After 1 hour, the blood level was 21070 pmol/l, compared to 900 pmol/l immediately before administration.

Next to none red fluid was discharged from the nose after administration to the subject. Both the pharmaceutical composition and the control were tolerated well, with only mild tingling in the nose. This compares very favourable to aqueous solutions of vitamin B12, that give an unpleasant experience.

As an aside, with cyanocobalamin and methylcobalamin no tingling was experienced, so it is believed that the pharmaceutical compositions according to the present invention will see better patient/recipient compliance.

The invention claimed is:

1. A method of administrating a pharmaceutical composition comprising:
   intranasally administrating the composition in a human subject for treatment of a condition,
   wherein the composition comprises vitamin B12 and a pharmaceutically acceptable carrier,
   wherein vitamin B12 particles are dispersed in a hydrophobic continuous phase as the pharmaceutically acceptable carrier; and
   wherein the condition is chosen from autism spectrum disorder, fatigue, memory deficiency, ALS, Alzheimer, deficiency caused by drug abuse, thinning of the stomach lining, vitamin B12 deficiency after surgery in which part of the stomach and/or small intestine is removed, Crohn's disease, celiac disease, Graves' disease, systemic lupus erythematosus and migraine.

2. The method according to claim 1, wherein the pharmaceutically acceptable carrier is selected from the group consisting of at least one of i) fat, ii) fatty acids, and iii) wax.

3. The method according to claim 1, wherein pharmaceutically acceptable carrier is oil.

4. The method according to claim 1, wherein the pharmaceutically acceptable carrier is an anhydrous pharmaceutically acceptable carrier.

5. The method according to claim 1, wherein the pharmaceutical composition comprises methylcobalamin or a pharmaceutically acceptable salt thereof as vitamin B12.

6. The method according to claim 1, wherein the concentration of vitamin B12 is in the range of 0.05-10 wt./vol. %.

7. The method according to claim 1, wherein vitamin B12 is colloidally dispersed.

8. The method according to claim 1, wherein the concentration of vitamin B12 is in the range between 0.4-8 wt./vol. %.

* * * * *